US006186004B1

United States Patent
Kaduchak et al.

(10) Patent No.: US 6,186,004 B1
(45) Date of Patent: Feb. 13, 2001

(54) APPARATUS AND METHOD FOR REMOTE, NONINVASIVE CHARACTERIZATION OF STRUCTURES AND FLUIDS INSIDE CONTAINERS

(75) Inventors: Gregory Kaduchak; Dipen N. Sinha, both of Los Alamos, NM (US)

(73) Assignee: The Regents of the University of California, Los Alamos, NM (US)

( * ) Notice: Under 35 U.S.C. 154(b), the term of this patent shall be extended for 0 days.

(21) Appl. No.: 09/323,175

(22) Filed: May 27, 1999

(51) Int. Cl.$^7$ .................................................. G01N 29/04
(52) U.S. Cl. ............................... 73/596; 73/649; 73/655
(58) Field of Search ........................... 73/596, 649, 655, 73/657, 645, 646, 627, 628; 367/87, 92

(56) References Cited

U.S. PATENT DOCUMENTS

| | | | |
|---|---|---|---|
| 4,046,477 | * 9/1977 | Kaule ....................................... | 73/596 |
| 4,265,122 | * 5/1981 | Cook et al. .............................. | 73/627 |
| 5,457,997 | * 10/1995 | Naruo et al. ............................ | 73/643 |
| 5,767,407 | 6/1998 | Sinha ....................................... | 73/579 |
| 5,859,915 | * 1/1999 | Norris ..................................... | 381/75 |
| 5,885,129 | * 3/1999 | Norris ..................................... | 446/405 |
| 5,889,870 | * 3/1999 | Norris ..................................... | 381/77 |
| 5,974,881 | * 11/1999 | Donskoy et al. ........................ | 73/579 |
| 6,011,855 | * 1/2000 | Selfridge et al. ....................... | 381/111 |

OTHER PUBLICATIONS

"Non–Destructive Analysis of Defects Using Structural Wave Propagation" by M. Staudenmann and M.B. Sayir, (http://www.lfm.mavt.ethz.ch/~staudenm/eval–2.html) 31–Jan–95/HTML–Version by Markus Staudenmann.
"The Interaction of Lamb Waves with Defects" by David N. Alleyne and Peter Cawley, IEEE Trans. Ultrasonics, Ferroelectrics, and Frequency Control 39,381 (1992).
"A High Precision Ultrasonic System for Vibration Measurements" by M.S. Young and Y.C. Li, Rev. Sci. Instrum. 63, 5435 (1992).
"Noncontact Measurement of Vibration Using Airborne Ultrasound" by Oliver Bou Matar et al., IEEE Trans. Ultrasonics, Ferroelectrics, and Frequency Control 45, 626 (1998).
"Laser Acoustic Spectroscopy for CW Verification" by Julio G. Rodriguez, Verification Technologies, First/Second Quarters (1992), p. 40.

(List continued on next page.)

Primary Examiner—Richard A. Moller
(74) Attorney, Agent, or Firm—Samuel M. Freund (57) ABSTRACT

An apparatus and method for the remote, noncontact evaluation of structures and containers at large distances (on the order of several meters) in air is described. The invention utilizes an air-coupled, parametric acoustic array to excite resonance vibrations of elastic, fluid-filled vessels and structural members. A nonlinear mixing process in the air medium transforms highly directional, narrow beamwidth higher acoustic frequencies into lower acoustic frequencies suitable for vibrational excitation of common structures. The parametric array also has an advantage for nondestructive evaluation applications in that it is capable of producing a broader bandwidth than typical linear devices, such as speakers and ultrasonic transducers. Typical carrier frequencies are in the 200 kHz range, and the sound field 3 m from the array has been demonstrated to have a bandwidth of greater than 25 kHz at a center frequency of 15 kHz. Vibrations have been excited in a fluid-filled, steel container at distances greater than 3 m from the array which are readily detected using a laser vibrometer in a fixed position relative to the acoustic array. It is demonstrated that the fluid contained within the steel vessel may be classified by analyzing the change in the response of the generated lowest-order, antisymmetric Lamb wave to changes in the interior fluid loading.

20 Claims, 9 Drawing Sheets

OTHER PUBLICATIONS

Nondestructive Evaluation (NDE) Tests on Chemical Weapons and Containers at Tooele Army Depot, DOE/ID–10346, Jul. 1991, p. 16).

"The Affordable Portable Laser Vibrometer" by Ometron, Inc. (Http://www.Ometron.com and http://www.ImageAutomation.com/Ometron).

"High Frequency Resonant Electromagnetic Generation and Detection of Ultrasonic Waves" by Katshuhrio Kawashima et al., Jpn. J. Appl. Phys. 33, 2837 (1994).

"The Audio Spotlight: An Application of Nonlinear Interaction of Sound Waves to a New Type of Loudspeaker Design" by Masahide Yoneyama et al., J. Acoust Soc. Am. 73, 1532 (1983).

"Parametric Array in Air" by Mary Beth Bennett and Davdt T. Blackstock, J. Accoust Soc. Am. 57,562 (1975).

* cited by examiner

APPARATUS AND METHOD FOR REMOTE, NONINVASIVE CHARACTERIZATION OF STRUCTURES AND FLUIDS INSIDE CONTAINERS

FIELD OF THE INVENTION

The present invention relates generally to nondestructive evaluation of structures and containers and, more particularly, to remote, noninvasive evaluation of structures and the contents of containers using ultrasound. This invention was made with government support under Contract No. W-7405-ENG-36 awarded by the U.S. Department of Energy to The Regents of the University of California. The government has certain rights in the invention.

BACKGROUND OF THE INVENTION

It is often necessary to obtain information concerning the liquid contents within sealed or otherwise inaccessible articles. Inaccessibility might arise as a result of hazardous conditions such as radioactivity or toxic vapors in the vicinity of the article under investigation, or where a container is filled with highly toxic or highly flammable materials and it would be unsafe to make measurements that require direct contact between instruments and the container. Typically, simple properties of the liquid contents, such as the sound speed, density and how attenuating the liquid is, are sufficient to identify and characterize various sub-classes of chemicals as is demonstrated in U.S. Pat. No. 5,767,407 for "Noninvasive Identification Of Fluids By Swept-Frequency Acoustic Interferometry," which issued to Dipen N. Sinha on Jun. 16, 1998. However, this and other techniques require direct physical contact between the sensor and the item to be interrogated.

An assessment of liquid level in a container is also of significance. The only non-contact technique that is currently in use is a nuclear technique that essentially provides a x-ray image, but requires a radioactive source which generates its own safety issues.

Structural integrity of storage containers, pipes, reaction vessels and other mechanical structures is another area of importance for remote measurement technology. It would be of substantial value to be able to remotely identify and locate cracks and other mechanical defects in container walls and structural members (see, e.g., "Non-Destructive Analysis Of Defects Using Structural Wave Propagation" by M. Staudenmann and M. B. Sayir, (http://www.lfm.mavt.ethz.ch/~staudenm/eval-2.html) Jan. 31, 1995/HTML-Version by Markus Staudenmann, and "The Interaction Of Lamb Waves With Defects" by David N. Alleyne and Peter Cawley, IEEE Trans. Ultrasonics, Ferroelectrics, and Frequency Control 39, 381 (1992)).

Often, ultrasonic nondestructive testing techniques require direct contact of an acoustic transduction device to excite the vibrational modes of the structure under evaluation. Likewise, direct contact of a receiving device is required to measure the response of the object. These requirements are reduced by immersing the structure in an efficient sound conducting fluid or by propagating an acoustic disturbance through a jet of fluid. Though these techniques are effective in a large number of applications, there are still many situations where direct contact or immersion are not feasible.

Remote excitation of low-frequency vibrations in mechanical structures and containers using linear sound producing devices such as speakers and ultrasonic air transducers is well known (see, e.g., "A High Precision Ultrasonic System For Vibration Measurements" by M. S. Young and Y. C. Li, Rev. Sci. Instrum. 63, 5435 (1992), "Noncontact Measurement Of Vibration Using Airborne Ultrasound" by Oliver Bou Matar et al., IEEE Trans. Ultrasonics, Ferroelectrics, and Frequency Control 45, 626 (1998), "Laser Acoustic Spectroscopy For CW Verification" by Julio G. Rodriguez, Verification Technologies, First/Second Quarters (1992), p. 40, and "Nondestructive Evaluation (NDE) Tests On Chemical Weapons and Containers At Tooele Army Depot, DOE/ID-10346, July 1991, p. 16). However, because of the large wavelength of sound at low frequencies, the sound cannot be selectively directed at a individual target so that the distance between the excitation source and the object to be investigated must be small. Moreover, such devices have low bandwidth that restricts the frequency band of interrogation, and the generated sound emanates in all directions due to a lack of directivity of the sound generator, which represents a potential nuisance to surrounding areas and may actually be a hazard to the operator because of the high intensities required. Laser detection of vibrations may be employed without a mirror having to be attached to the object under investigation (see, e.g., "The Affordable Portable Laser Vibrometer" by Ometron, Inc. (http://www.Ometron.com and http://www.ImageAutomation.com/Ometron)).

Recent advances in noncontact nondestructive evaluation of materials include laser-generated sound and electromechanical acoustic transduction devices (EMATs). However, EMATs are required to be located only a short distance from an object under investigation (see, e.g., "High Frequency Resonant Electromagnetic Generation And Detection Of Ultrasonic Waves" by Katsuhrio Kawashima et al., Jpn. J. Appl. Phys. 33, 2837 (1994)), and laser-generated sound techniques require high optical power levels to generate detectable ultrasonic disturbances which render it problematic in situations where the material under investigation is unstable.

In "The Audio Spotlight: An Application Of Nonlinear Interaction Of Sound Waves To A New Type Of Loudspeaker Design" by Masahide Yoneyama et al., J. Acoust Soc. Am. 73, 1532 (1983), and in "Parametric Array In Air" by Mary Beth Bennett and David T. Blackstock, J. Acoust Soc. Am. 57, 562 (1975), an audio signal produced from an amplitude-modulated ultrasound primary wave radiated from a transducer array into air due to the self-demodulation effect from nonlinear mixing by the air, and the generation of a difference-frequency signal from the interaction of two collinear primary sound beams from a parametric array, respectively, are described. However, neither paper teaches the use of the low-frequency audio signal for analysis of structures or the contents thereof.

Accordingly it is an object of the present invention to provide an apparatus and method for nondestructively and remotely analyzing the integrity of structures and the contents of containers.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus for remote, noninvasive characterization of an object hereof may include: at least one air-coupled transducer for generating a directed, ultrasonic sound wave having a chosen frequency, and disposed at a chosen distance from the object to be characterized; modulation means for amplitude modulating the ultrasonic sound wave at a chosen modulation frequency, whereby the amplitude modulated ultrasonic sound wave interacts with the air between the object and the transducer thereby generating an acoustic wave having lower frequency than the ultrasonic sound wave capable of exciting vibrational motion in the object; and remote means for measuring the vibrational excitation in the object, whereby the object is remotely characterized.

In another aspect of the present invention, in accordance with its objects and purposes, the apparatus for remote, noninvasive characterization of an object hereof may include: at least one first air-coupled transducer for generating a first directed, ultrasonic sound wave having a chosen first frequency and disposed at a first chosen distance from the object; at least one second air-coupled transducer for generating a second directed, ultrasonic sound wave having a chosen second frequency, and disposed at a second chosen distance from the object, whereby the first sound wave and the second sound wave are caused to intersect in the air between the first transducer and the second transducer and the object, such that the difference frequency therebetween is generated and impinges on the structure, thereby producing vibrational excitation in the object; and remote means for measuring the vibrational excitation in the object, whereby the object is remotely characterized.

In yet another aspect of the present invention, in accordance with its objects and purposes, the method for remote, noninvasive characterization of an object hereof may include the steps of: generating a directed, ultrasonic sound wave having a chosen frequency, wherein the ultrasonic sound wave is directed toward the object to be characterized; amplitude modulating the ultrasonic sound wave at a chosen modulation frequency, whereby the interaction of the amplitude modulated sound wave with the air medium generates a sound wave having as its frequency the chosen modulation frequency which produces vibrational excitation in the object; and remotely measuring the vibrational excitation in the object, whereby the structure is remotely characterized.

In still another aspect of the present invention, in accordance with its objects and purposes, the method for remote, noninvasive characterization of an object hereof may include the steps of: generating a first directed, ultrasonic sound wave having a chosen first frequency and directed toward the object to be characterized; generating a second directed, ultrasonic sound wave having a chosen second frequency, and directed toward the object, whereby the first sound wave and the second sound wave are caused to intersect in the air such that the difference frequency therebetween is generated and impinges on the object, thereby producing vibrational excitation in the object; and measuring the vibrational excitation in the object, whereby the object is remotely characterized.

Benefits and advantages of the present invention include remote, noncontact monitoring the contents of waste and biological material storage containers and container wall integrity, remote, noncontact determination of the contents of ordnance, remote, noncontact monitoring of reactor vessels and pipes for process control, determining liquid-fill level in tanks, and inspection of airplane wings, without having to immerse the articles under investigation in water or use water-jets to provide transducer coupling.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings:

FIG. 6a is a graph of the calculated, phase velocity of Lamb waves propagating on an infinite cylinder with the dimensions and material properties of the cylindrical container shown in FIGS. 4a and 4b hereof, as a function of frequency, the shift in the propagation velocities being the result of different fluids contained in the cylinder, while

DETAILED DESCRIPTION

Briefly, the present invention includes an apparatus and method for the remote characterization of mechanical structures and the fluid contents of containers using an air-coupled parametric array disposed at large distances from the structures or vessels to be investigated. The invention is based on nonlinear mixing of highly directional, high-frequency sound waves in the air transport medium for generating lower-frequency sound waves capable of exciting vibrational motion in the object under investigation such as a container or other vessel, pipes, etc. Two procedures for achieving this effect are described. In the first, a modulated ultrasonic carrier wave is directed toward the object under investigation in an air medium, the modulation frequency being varied in order to generate a variable frequency sound wave which interacts with the object, while the second requires two sources of ultrasonic sound waves which are caused to intersect in the vicinity of the object, the relative frequency of the sound waves being varied in order to generate a variable frequency sound wave which interacts with the object. Optical detection of the vibrational excitation of the container provides information about the container and its contents as a result of the fluid-container interaction. Identification of chemicals inside sealed containers is demonstrated. The present invention is well suited for use in hazardous conditions where direct contact with containers is neither possible nor desired. In addition, the invention can be used for determining integrity of mechanical structures, including walls of a container, for defects. By contrast to linear acoustical devices, such as speakers and ultrasonic transducers, nonlinear sound generation is capable of producing directed sound beams and has significantly broader frequency bandwidths. An additional advantage of the present apparatus and method is that the projected sound is only audible in the direct beam path and not elsewhere.

Plate waves are remotely generated in the wall of the structure under investigation and the interaction of these waves with the structure of with the contents therein are remotely measured using vibration sensor, such a laser Vibrometer. In the situation where a fluid container is to be interrogated, the container wall-fluid interaction contains the information regarding fluid sound speed, density, and fluid sound attenuation. This information is in the form of a spectrum with a series of resonance peaks. For example, for a cylindrical geometry, when an integral number of full-wavelengths span the circumference, the plate waves (guided waves) establish a standing wave for each integer where this resonance condition is fulfilled. Guided wave speeds are frequency dependent and therefore the resonance peak spacing changes with frequency. If the wall material and container contents are known, resonance peak spacing provides information about the thickness of the wall. In particular, changes in wall thickness due to corrosion or other chemical processes can be detected. The presence of liquid inside the container affects the observed resonance pattern by shifting it in frequency that depends on both liquid sound speed and liquid density. Liquid attenuation may be determined through change in resonance Q (sharpness), while liquid level can be determined by monitoring the amplitude of any observed resonance peak as the laser beam utilized to measure container wall vibrational amplitude is moved in a vertical direction over the container surface. When the laser beam passes through the location of the liquid within the container, the amplitude of vibration monitored by the Vibrometer changes.

In a first embodiment of the present invention, two, high-frequency ultrasonic beams are directed such that they intersect in front of the target. Because of nonlinear mixing of in air, sum and difference frequencies are generated in the intersecting volume. For example, if one beam has a frequency of 200 kHz and the other has a frequency of 210 kHz, a difference frequency of 10 kHz and a sum frequency of 410 kHz will be generated. The high frequencies are attenuated as they propagate through the air, whereas the lower difference frequencies can continue propagating in the forward direction. This low frequency can then resonantly interact with the target. It should be mentioned that a plurality of interacting ultrasonic beams can be employed. Although the acoustic impedance between air and any kind of solid container is large, the sound couples with the target through resonant interaction and launches guided waves, which circumnavigate the target. The initial high frequencies provide directionality of the launched sound wave beam, and by sweeping the frequency of one of the beams it is possible to obtain the resonance spectrum of the target over wide a range of frequencies.

In a second embodiment of the invention, a single source (which may be constituted of a large number of smaller independent sources) is driven at a high frequency (for example, at 200 kHz) but is amplitude modulated at the desired low frequency (or swept frequency). As this amplitude-modulated beam propagates, the nonlinearities in the air interaction and absorption by the air down-convert the modulated signal so that after a distance, only the low-frequency modulating signal remains, while the high-frequency carrier signal disappears. This second embodiment has been determined to be more efficient than the first embodiment hereof. The remainder of the measurement procedure is the same as described hereinabove. Both embodiments have been reduced to practice.

Interior fluid classification is achieved by analyzing the propagation characteristics of the guided waves (for example, the lowest-order generalized antisymmetric Lamb wave, $a_o$) which is guided by the circumference of the container. The $a_o$ Lamb wave is in a class of guided waves which exhibit strong flexural vibrations near the coincidence frequency of the container. This equates into large radial displacements of the container wall. Thus, by analyzing the propagation characteristics of the $a_o$ Lamb wave, it is possible to detect changes in inertial loading on the interior wall of the container which yields insight into the identity of the fluid contained within the vessel. Classifications can also be made by analyzing the structural response for any guided wave. Which waves are actually excited in an object is dependent on the geometry and physical properties of the object, and the frequency of excitation.

A commercial laser vibrometer having an effective range of 20 feet was employed to remotely measure vibrations. There are other commercially available devices that have ranges exceeding 30 feet.

The observed resonance pattern changes in a predictable manner with changes in liquid sound speed and density, and these parameters can be readily determined. The sharpness of the resonance (damping, full-width-at-half-maximum) depends on the liquid sound attenuation and can be determined from the spectrum. As described hereinabove, the laser beam impinging on the container is moved in a vertical direction gradually and its amplitude monitored. As the beam crosses the location of the liquid level within the container, the resonance amplitudes change dramatically. It is also possible to lock onto a single resonance peak frequency using conventional electronics and monitor its amplitude as the laser beam is moved vertically along the surface of the target.

Since the waves propagating along the perimeter of the container are plate waves and not simply surface waves, if there are cracks or other defects in the wall, the propagation of these waves is affected and can be observed in the spectrum. In general, the observed spacing between the features of the resonance pattern increases with increasing frequency for $a_0$-wave excitation. When defects are present, this pattern is altered and can be detected.

Having generally described the invention, the following EXAMPLE will provide additional details thereof.

EXAMPLE

Parametric excitation of an acoustic field is a process which utilizes the nonlinearity of a host medium for the creation of secondary sound sources. Two finite amplitude sound beams interact to create secondary frequency components which correspond to the sum and difference of the original excitation frequencies (see, e.g., "Nonlinear Effects In sound Beams" by M. F. Hamilton, *Handbook Of Acoustics*, M. J. Crocker ed. Wiley, New York, 1998). For typical applications in air, where absorption rapidly increases with frequency, the high-frequency, sum-frequency components attenuate rapidly as a function of propagation distance leaving only the difference-frequency components of the sound field (see, e.g., "Atmospheric Absorption Of Sound: Further Developments" by H. E. Bass, J. Acoust. Soc. Am. 97, 680 91995). This results in a broad-bandwidth acoustic source which operates at the difference frequency. Such a source has a broad bandwidth since the bandwidth of the excitation transducers scales with their resonance frequency. As a simple example, consider two transducers with center frequency 200 kHz. Assuming that each is capable of achieving a 20% bandwidth about its center frequency, each transducer efficiently excites an acoustic disturbance in the frequency range 180 kHz<f<220 kHz. If used together in a parametric sound source, the excitation frequencies of these transducers may be adjusted to create a difference-frequency sound field in the frequency range 0<f<40 kHz. This is in contrast to an acoustic source with center frequency at 10 kHz. A 20% bandwidth for this source yields an acoustic source capable of sound production in the frequency range of 9 kHz<f<11 kHz.

Figure 1:
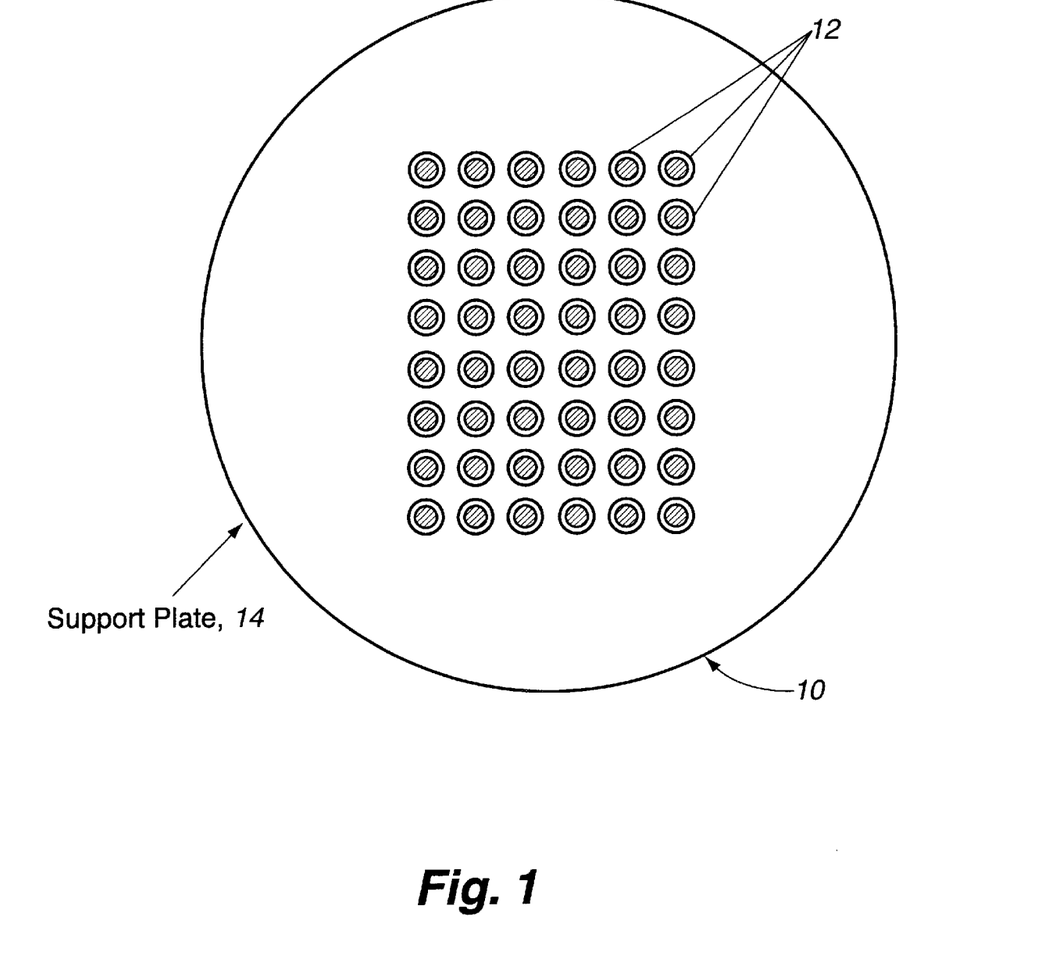
FIG. 1 is a schematic representation of the acoustic parametric array of the present invention illustrating 48 air-coupled transducers, each having resonance frequency at 200 kHz.

Reference will now be made in detail to the present preferred embodiments of the invention examples of which are illustrated in the accompanying drawings. Similar or identical structure therein is identified by identical callouts. The parametric array used in the demonstration of the apparatus of the present invention is constructed using commercial, off-the-shelf, air-coupled acoustic transduction devices each having a nominal resonance frequency of 200 kHz. Frequencies from 40 kHz to 1 MHz can be employed depending on the intended application. The upper frequency is determined by the distance between the transducer array and the structure under investigation, since air absorbs higher acoustical frequencies, while the lower frequency is dictated by how narrow an interrogating beam is desired. Moreover, a transducer array can be configured to focus the interrogating beam onto the structure in order to distinguish it from other, nearby structures. Turning now to the drawings, FIG. 1 is a schematic representation of the acoustic parametric array, 10. It is comprised of 48 air-coupled, commercially available transducers, 12, each transducer having an actual resonance center frequency at 217 kHz. Practically any type of air-coupled transducers can be used, capacitive transducers, for example, and an arbitrary number of transducers may be employed; the number of transducers used depends on the power required to be transmitted to the target. It should be mentioned that the present invention can also be operated in the tone burst mode, where short bursts of sinusoidal sound waves are employed.

Each transducer is driven in parallel using a sinusoidal signal having a peak-to-peak amplitude of 20 V from a wideband power amplifier (not shown in FIG. 1). In the situation where two series of transducers are driven at slightly different frequencies, the low-frequency sound generated by the two arrays is spectrally described by the difference frequency of the two fields. The individual transducers are partially inserted into holes disposed in a Delrin plate, 14, one transducer per hole, in order to provide some channeling for the ultrasound as a result of the small cylindrical cavity formed in front of each transducer, and spaced apart by approximately 19 mm. The aperture dimension of the array in the horizontal direction is approximately 11.1 cm and the aperture dimension in the vertical direction is approximately 14.9 cm. In accordance with the teachings of the present invention, the secondary sound field is generated at the difference frequency of two closely spaced frequency components (e.g. $|f_1-f_2|$<30 kHz). The biharmonic sinusoid driving voltages give rise to sum and difference frequencies proportional to:

$$v(t)=\cos(2\pi f_1 t)+\cos(2\pi f_2 t)=2\cos(2\pi(f_1-f_2)t)\cos(2\pi(f_1+f_2)t)=2\cos(2\pi f_d t)\cos(2\pi f_s t) \qquad (1)$$

(see, e.g., *Nonlinear Wave Processes In Acoustics* by K. Naugolnykh and L. Ostrovsky, Cambridge University Press, pp. 165–188 (1998)).

The array of transducers is driven with a voltage described by sum frequency $f_s$=217 kHz and difference frequency: 2 kHz<$f_d$<30 kHz. Measurements performed at 0.5 m from the array yielded a sound pressure level of approximately 115 dB at the sum frequency. At lengths where the high frequency has been severely attenuated by air absorption (at the target approximately 3 m from the source), measurements performed at the difference frequency yielded a sound pressure level of approximately 85 dB.

Figure 2:
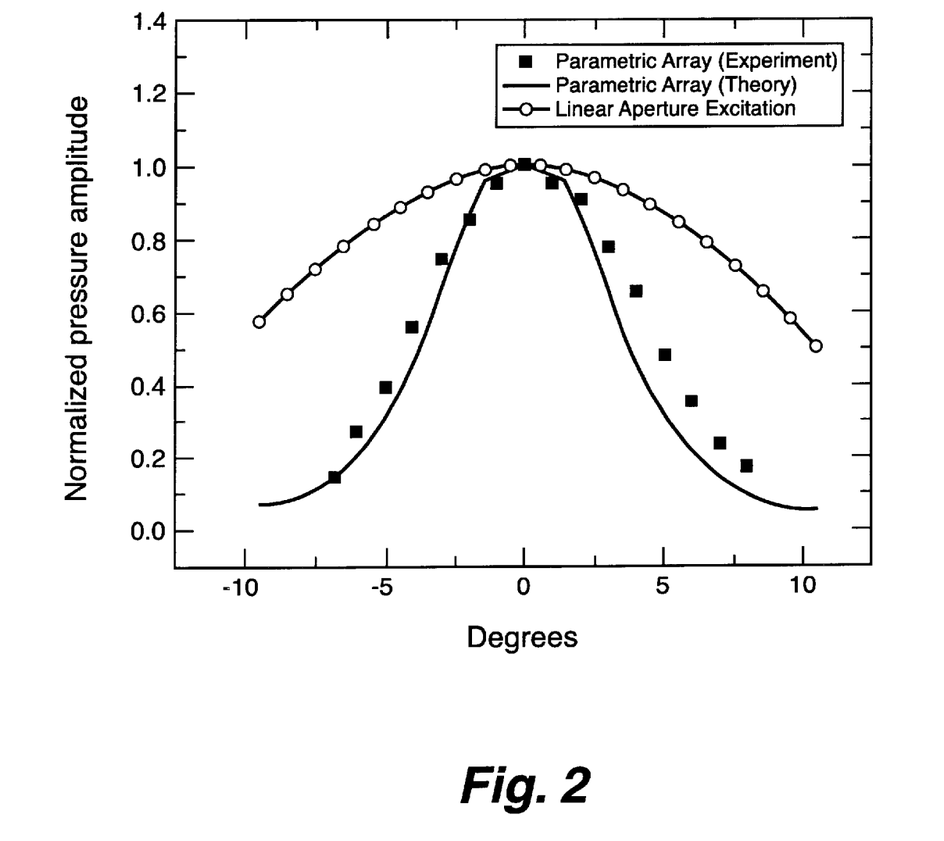
FIG. 2 is a graph showing the measured and theoretical ultrasound emission patterns for the parametric acoustic array shown in FIG. 1 hereof for a difference frequency of 13 kHz, as a function of degrees measured from the center of the emission, while the data represented by the hollow circles is the directivity pattern for an array of the same dimension driven by a sinusoidal input at the difference frequency.

The difference frequency field is generated along the propagation path of the primary field. The creation of the field is a volume interaction which may be described as a continuous secondary source which extends along the path of propagation of the primary field. The beamwidth of this type of source can be extremely narrow relative to a field produced by driving the source aperture with the difference frequency. This is displayed in FIG. 2, which is a graph illustrating the ultrasound emission pattern for the parametric acoustic array shown in FIG. 1 hereof at a difference frequency of 13 kHz. Measurements of the difference frequency field are represented by the solid squares, and the pattern predicted by theoretical analysis is represented by the solid line. The curve having hollow circles is the emission pattern for an array having the same dimension as the parametric array which is driven by a sinusoidal input at the difference frequency. The solid squares represent experimental measurements taken at a distance of 4 m from the array. The hollow circles represent the calculated beam pattern for an aperture of the same dimension driven at the difference frequency. It is obvious from the figure that parametric production of sound displays a much narrower beam pattern than conventional arrays which operate under linear principles for the same aperture size.

Figure 3A:
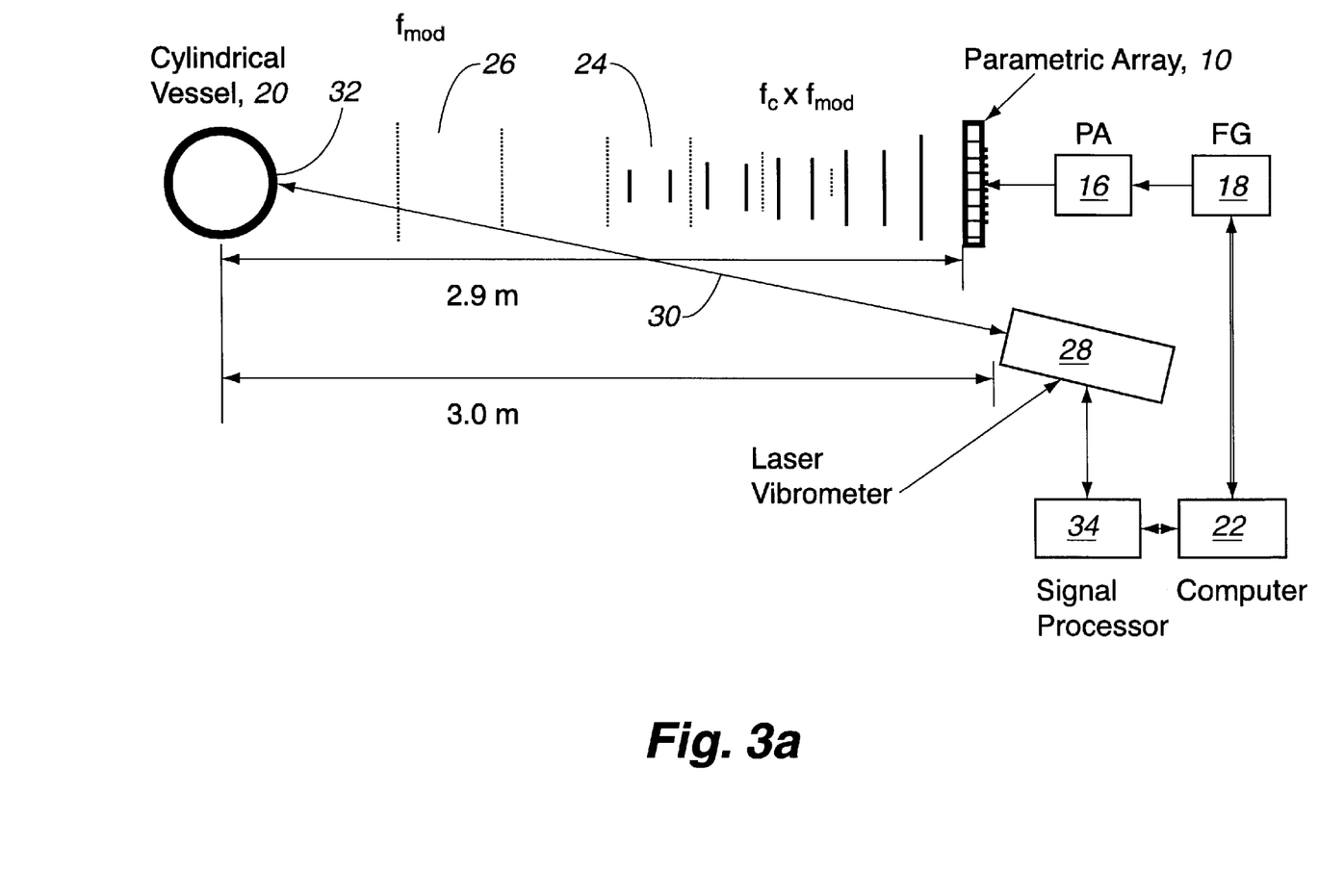
FIGS. 3a and 3b are a schematic representations of two embodiments of the apparatus of the present invention utilizing the parametric array shown in FIG. 1 hereof for the classification of fluids in containers, FIG. 3a showing an amplitude-modulated parametric array and FIG. 3b showing two parametric arrays having interacting ultrasonic beams at slightly different frequencies.
Figure 3B:
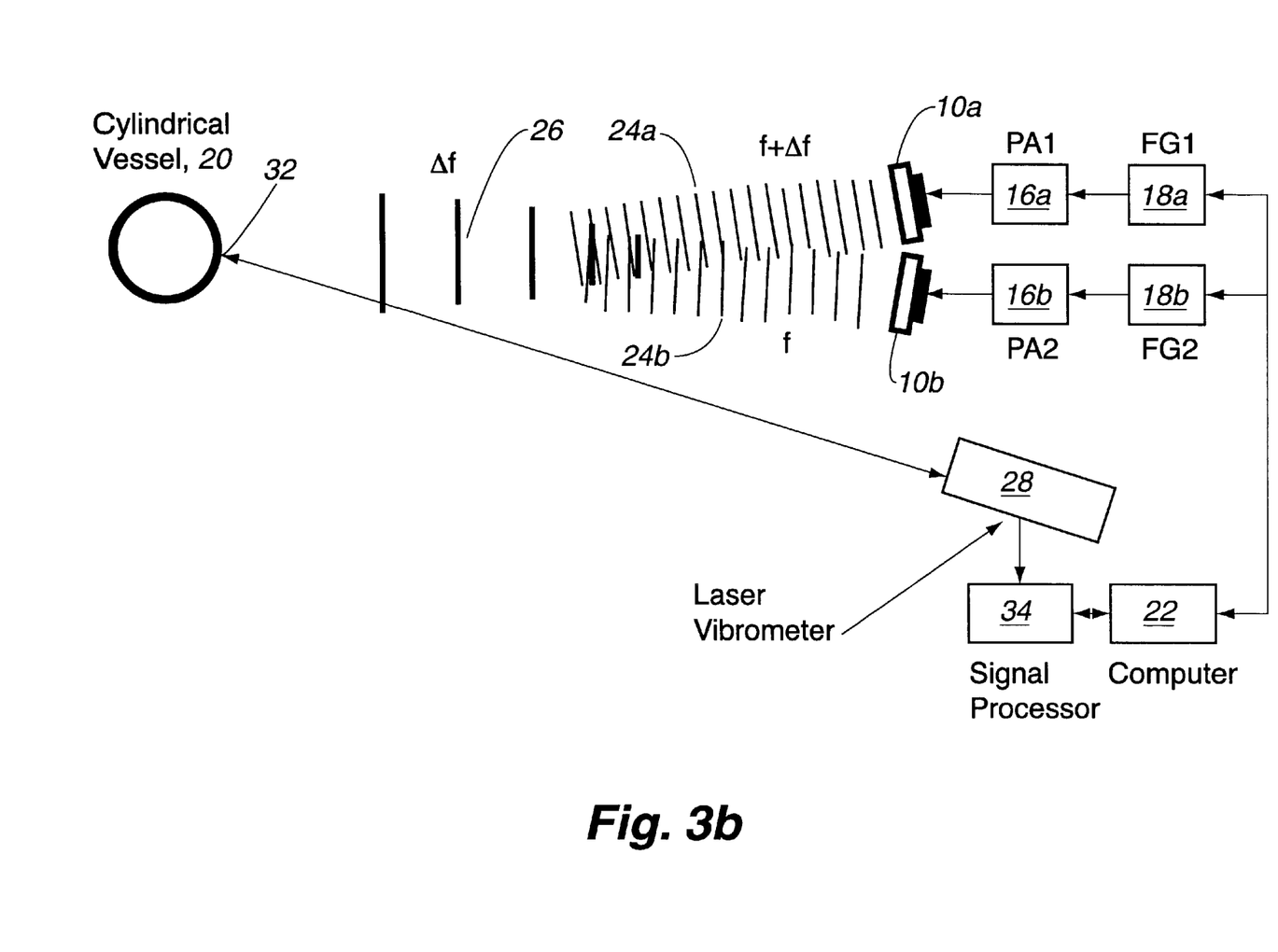

FIGS. 3a and 3b hereof illustrate two embodiments of the apparatus used to demonstrate the present invention. FIG. 3a shows the embodiment of the present invention where a single parametric array 10, powered by wideband power amplifier, 16, driven by a digitally controlled, modulatable and sweepable function generator, 18, is placed at a distance of approximately 3 m from a sealed, steel container, 20. The function generator provides a modulated sine-wave output having a carrier frequency which matches the center frequency of the transducers. Computer, 22, controls the amplitude of the modulating frequency and varies this frequency between 1 and 30 kHz in steps of, say, 10 Hz over a period of time between 10 and 30 seconds in duration. Ultrasonic radiation from array 10 having a carrier frequency and a range of modulation frequencies (1 kHz<$f_d$<30 kHz) then travels through air conduit, 24. A narrow acoustic beam, 26, of demodulated sound having the modulation frequency (1–30 kHz) of the parametric array reaches vessel 20, since the carrier frequencies are absorbed by the air during transit. The beam excites the vibrational resonances of the container. In the present example, the vibrational response is due to circumferential resonance of the lowest order antisymmetric Lamb wave on the structure—$a_o$ Lamb wave.

This vibrational response of container 20 is measured using a commercially available laser vibrometer, 28, which is disposed a similar remote distance to that of acoustic source 10. The laser vibrometer employed was a Doppler device which measures the velocity of the vibrating container wall by detecting the Doppler shift in the reflected light beam; thus, observed spectral data are proportional to the velocity of the vibrating wall. The spatial resolution of the focused laser beam, 30, on the cylindrical surface, 32, of container 20 is approximately 0.5 mm. The signal from the vibrometer was detected at the modulating frequency using two types of signal-processing apparatus, 34. For one, a digital lock-in amplifier was employed; for the second approach, a signal processing circuit that uses a narrow-band (100 Hz) band-pass tracking filter driven by the modulating frequency signal was employed. Thus, in each apparatus, the vibration signal measured by laser vibrometer 28 was evaluated only at the frequency of excitation (modulation frequency) and within a very narrow bandwidth. This provided a very high signal-to-noise ratio and easier detection of the resonances. Computer 22 controlled the modulating frequency input to the function generator. It also simultaneously controlled the center frequency of the tracking filter. In the case of the lock-in amplifier, the modulating frequency output of the function generator was used as the reference signal and this allowed automatic tracking. The output of the lock-in amplifier was read into the computer through an interface, while in the case of the tracking amplifier, the analog output of the filter was digitized at 14-bit and then read into the computer through the parallel port. By analyzing the shift in the circumferential resonance frequencies of the $a_o$ Lamb wave as the fluid is changed within the vessel, it is possible to classify the fluid.

FIG. 3b is a schematic representation of the embodiment of the invention using two ultrasonic beams. The transducers from each of two smaller-size, essentially identical arrays, 10a and 10b, were electrically connected in parallel and driven from independent power amplifiers, 16a and 16b, using two independent function generators, 18a and 18b. Each of these power amplifiers has the capability to provide a DC bias of up to 200 V which is necessary if capacitive transducers are used. The frequency of one function generator is kept fixed whereas the frequency of the second generator is varied by computer 22 in small steps (say, in 10 Hz increments over the range of modulation frequencies $f_d$, where the time interval between steps is much greater than the characteristic time to establish circumferential resonances in the container) over a period of time to produce a frequency sweep. As in the single array embodiment, only a low-frequency (in this situation, the difference frequency) ultrasound signal reaches the surface 32 of container 20. When the tracking filter is used, the center frequency of the filter is controlled by the computer as well and everything stays locked to the excitation frequency of the target that is produced by the mixing of the two beams at two frequencies. For example, one transducer array is driven at a fixed 200 kHz frequency, whereas the other array is swept from 201 to 230 kHz.

When the lock-in amplifier is utilized for the signal detection in the two-beam approach, the difference frequency is required for the lock-in reference, and an analog frequency mixer followed by a low-pass filter where the output of the two function generators is mixed to obtain this frequency is used as the lock-in reference input. It should be mentioned that the first embodiment was found to be more efficient than the second, since the mixing volume is much greater for this embodiment.

Figure 4A:
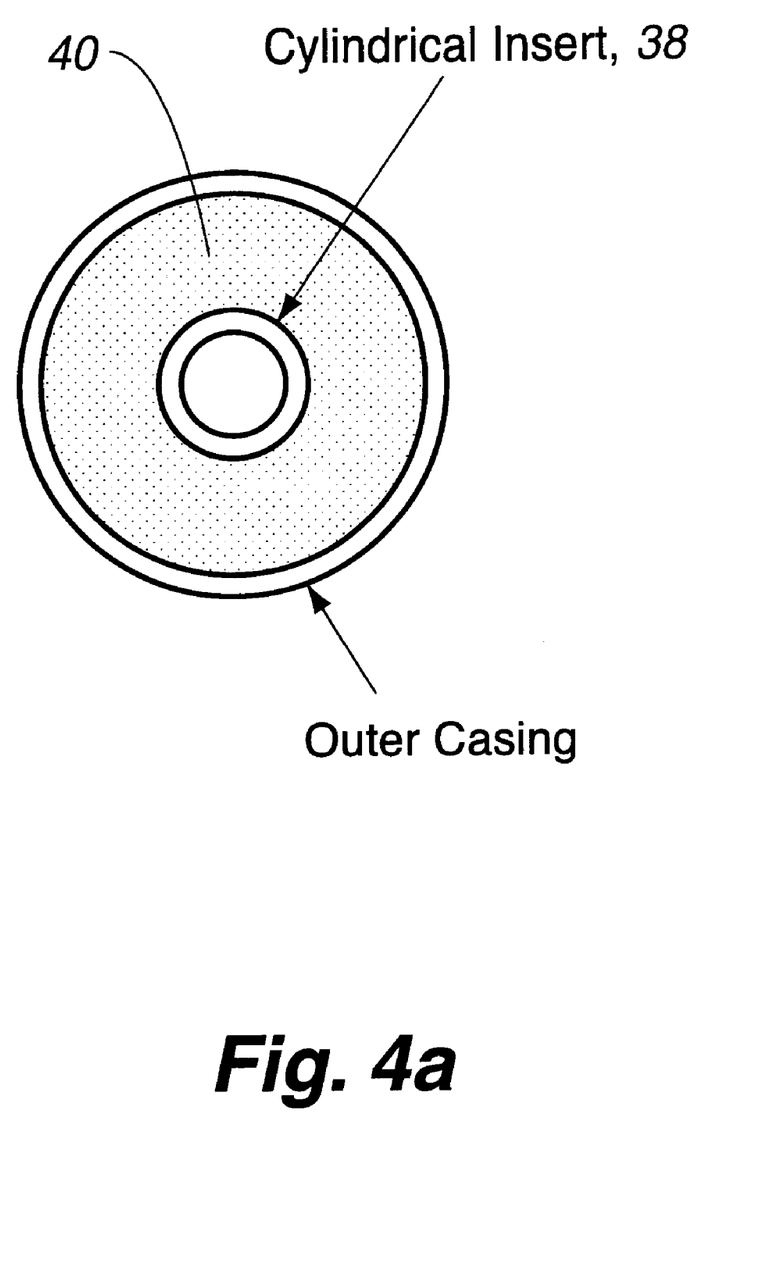
FIGS. 4a and 4b are schematic representations of the top view and side view, respectively, of a fluid-filled container used to demonstrate the apparatus of the present invention.
Figure 4B:
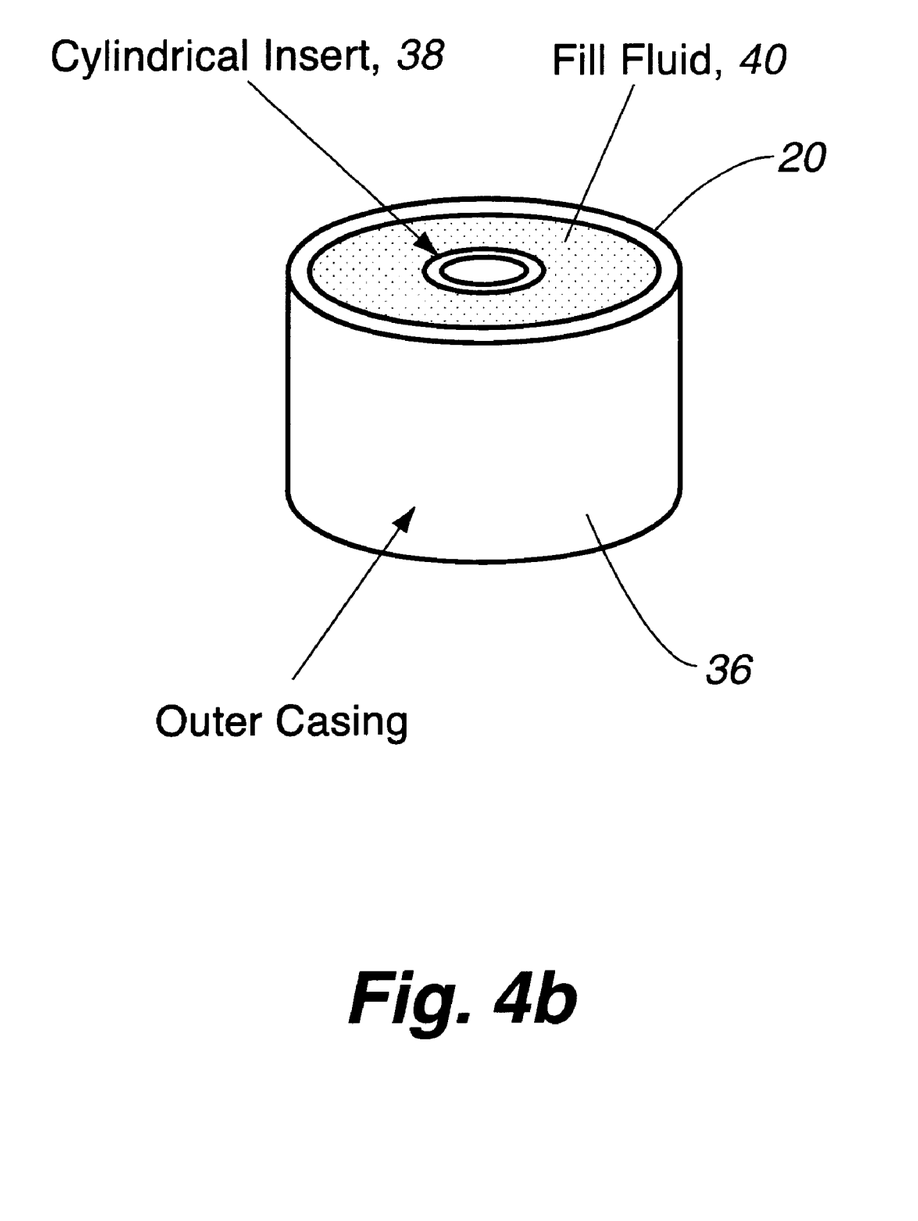

FIGS. 4a and 4b, hereof are schematic representations of the top view and side view, respectively, of the vessel utilized to demonstrate the apparatus of the present invention. The vessel has an outside diameter of 15.1 cm, a wall, 36, thickness of 0.5 cm, and height 12.7 cm. There is a cylindrical, steel structure, 38, coaxial with the center of vessel 20 having a diameter of 4.4 cm, thereby defining an annular cavity, 40, which was filled with either ethylene glycol or isopropanol. The reason for this is that chemical-agent-filled artillery shells having a burst core were intended to be simulated. It is expected that internal cylinder 38 has a negligible effect on the vibratory response of the external wall of the container. The approximate elastic properties of the vessel and its contents are provided in the TABLE.

TABLE

| Material | Density (g/cc) | Longitudinal velocity (m/s) | Shear velocity (m/s) |
|---|---|---|---|
| Steel | 7.85 | 5980 | 3360 |
| Air | 0.0012 | 340 | |
| Isopropanol | 0.786 | 1170 | |
| Ethylene Glycol | 1.11 | 1660 | |

Figure 5:
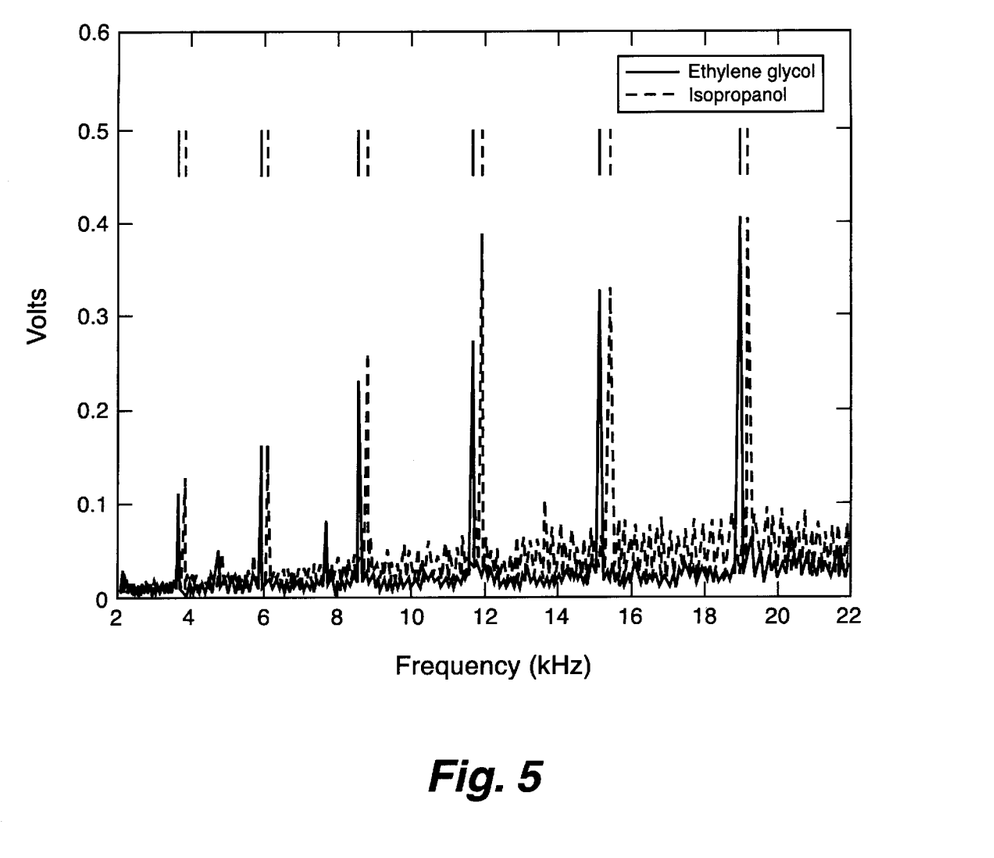
FIG. 5 shows the spectral response of identical steel vessels containing either ethylene glycol or isopropanol, where the large, regular peaks correspond to Lamb wave resonances which propagate along the circumference of the container and which shift in frequency dependent on the interior loading materials.

FIG. 5 is a graph of the resonance response of two fluid-filled steel vessels when excited using the single, modulated parametric array at a distance of 3 m. The large, regular peaks correspond to circumferential resonances of the $a_o$ Lamb wave propagating along the circumference of the container. The spectral shifts in the peaks identify different interior loading conditions and thus are used as a classification tool. The short vertical lines correspond to the locations of the circumferential resonances of the $a_o$ Lamb wave calculated for an infinite cylinder with the same dimensions and material properties of the cylindrical container in the experiments. The difference between the two containers employed is that each is filled with a different fluid: either isopropanol or ethylene glycol, the physical properties of which are listed in the TABLE. The vertical axis of FIG. 5 is the signal generated by the laser vibrometer and is proportional to the velocity of the vibrating container wall. The horizontal axis represents the difference-frequency of the modulated, transmitted 217 kHz carrier wave. From FIG. 5 it is clear that the major spectral features (the rather distinct 'spikes') are shifted relative to one another. The frequency shift varies from 142 Hz near 3.7 kHz, to approximately 274 Hz near 19.3 kHz. To confirm that these spectral shifts were not an artifact of differences in the containers, measurements were made on one of the containers alternately filled with isopropanol and ethylene glycol. The difference between those results and the results presented in FIG. 5 were found to be negligible.

It is shown in FIG. 5 that the fluid loading affects the resonance response of the cylindrical vessel. The resonance frequencies are shifted to slightly lower values for the ethylene glycol filler relative to isopropanol. This shift is a result of the difference in the interior fluid loading conditions on the internal wall of the container. Increased inertial loading decreases the measured resonance frequencies which is demonstrated by the downward shift in the resonance frequencies for the 'heavier' ethylene glycol.

Figure 6A:
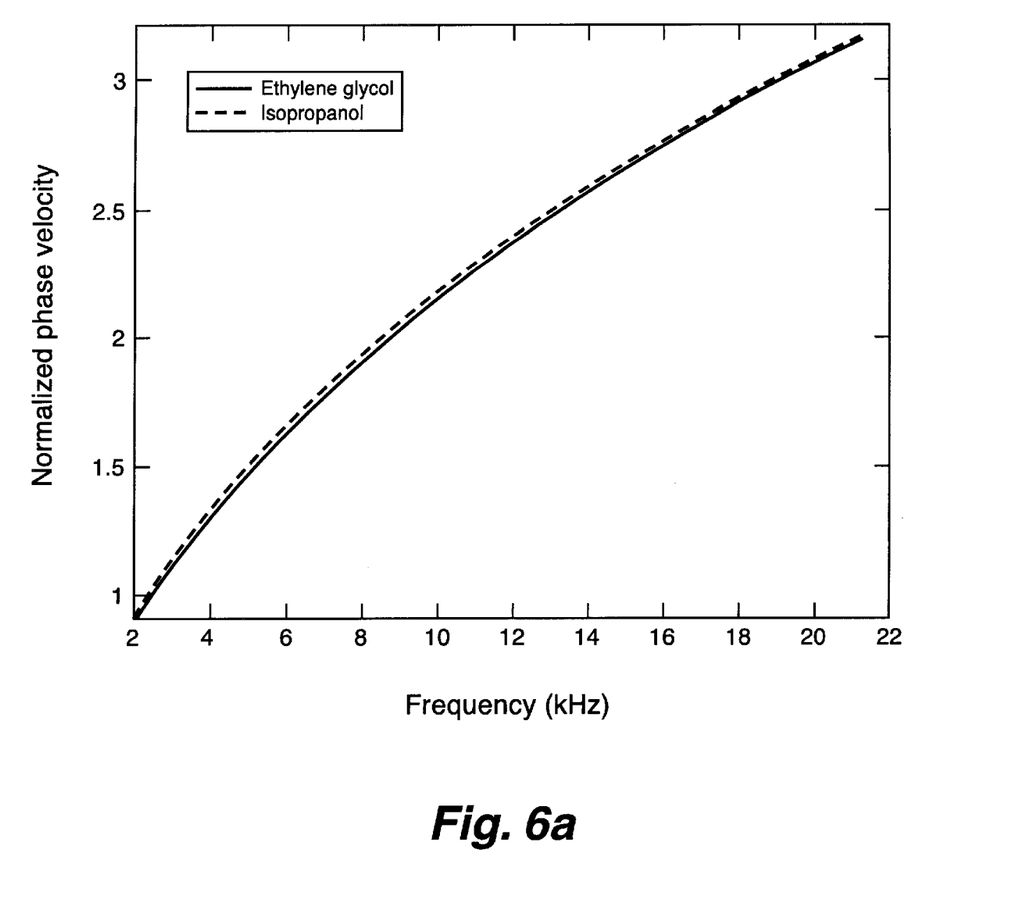

FIG. 6a shows the calculated phase velocity of the $a_o$ Lamb wave for circumferential propagation around an infinite cylinder with the same material parameters as the cylindrical containers described hereinabove. The curves were calculated with the complex mode number methodology of the Sommerfeld Watson Transformation for an infinite cylinder externally fluid-loaded by air (see, e.g., "Ray Synthesis Of Leaky Lamb Wave Contributions To Backscattering From Tick Cylindrical Shells" by N. H. Sun and P. L.

Figure 6B:
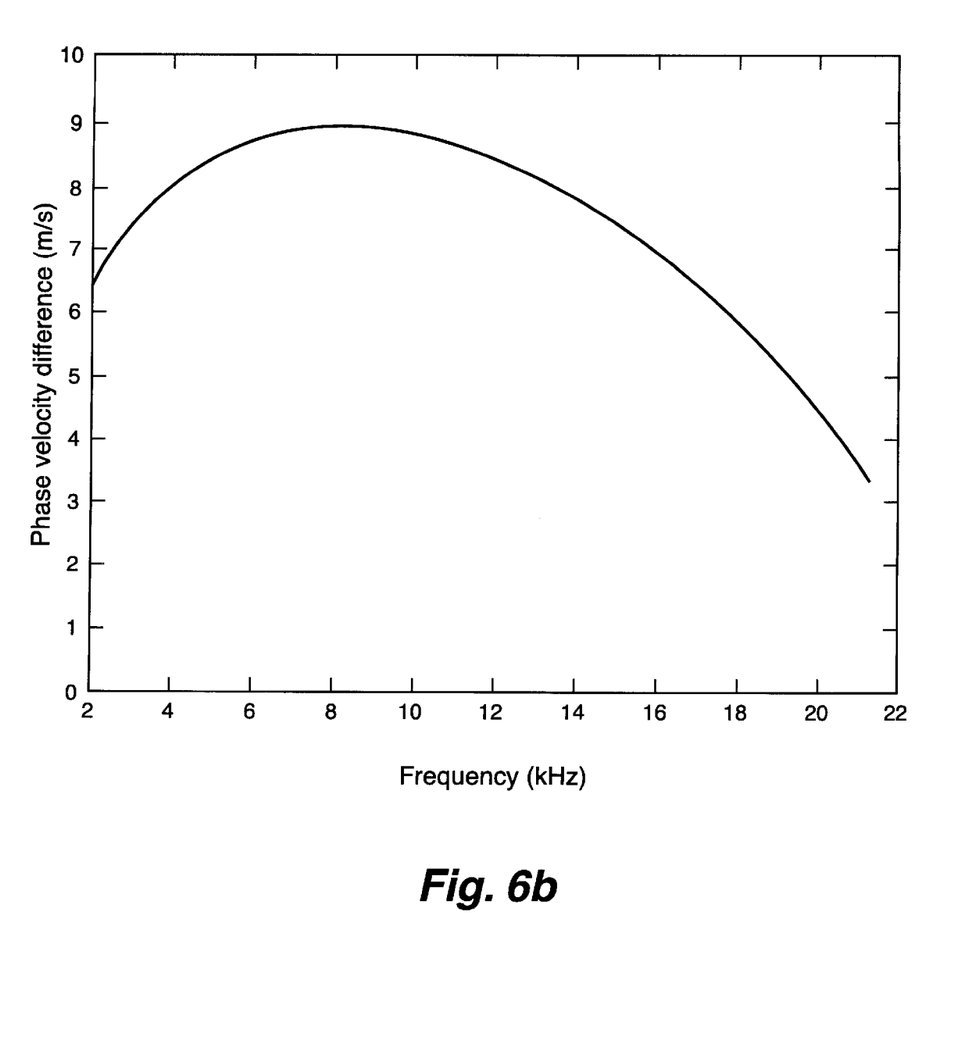
FIG. 6b is a graph showing the difference in the phase velocities for the two liquids as a function of frequency.

Marston, J. Acoust. Soc. Am. 91, 1398 (1992)). The dashed line in the figure displays the phase velocity of the $a_o$ Lamb wave for interior fluid loading of ethylene glycol, while the gray line represents the phase velocity of the $a_o$ Lamb wave for interior fluid loading of isopropanol. The phase velocities are slightly different for the two different interior loading conditions and are the result of different fluid loading conditions on the interior wall of the cylinder. FIG. 6b is a graph showing the difference in the phase velocities for the two liquids as a function of frequency.

The circumferential resonance condition for a cylindrical shell is related to the phase velocity of the elastic disturbance $$f_{res} = \frac{nc_1}{2\pi a}, \quad (2)$$

where a is the radius of the container, $c_l$ is the phase velocity of the disturbance on the cylinder, and n is a positive integer corresponding to the number of full wavelengths required to span the circumference of the vessel. Using the values of the phase velocity from FIGS. 6a and 6b, hereof, the circumferential resonance locations are shown as the short vertical lines in FIG. 5 for comparison with the experimental data, and demonstrate good agreement between the measured and calculated values for the resonance frequency shifts due to changes in the interior loading conditions.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for remote, noninvasive characterization of an object which comprises in combination:
    (a) at least one air-coupled transducer for generating a directed, ultrasonic sound wave having a chosen frequency, wherein the ultrasonic sound wave is directed toward the object to be characterized;
    (b) modulation means for amplitude modulating the ultrasonic sound wave at a chosen modulation frequency, whereby the interaction of the amplitude modulated sound wave with the air medium between the object to be characterized and said at least one transducer generates a sound wave having as its frequency the chosen modulation frequency, the sound wave produced thereby generating vibrational excitation in the object to be characterized; and
    (c) remote means for measuring the vibrational excitation in the structure under investigation, whereby the object is remotely characterized.

2. The apparatus for remote, noninvasive characterization of an object as described in claim 1, wherein said remote means for measuring the vibrational excitation includes a laser vibrometer.

3. The apparatus for remote, noninvasive characterization of an object as described in claim 1, wherein said at least one air-coupled transducer is disposed at a sufficient distance from the object to be characterized such that a substantial portion of the directed ultrasonic sound wave is absorbed by the air therebetween.

4. The apparatus for remote, noninvasive characterization of an object as described in claim 1, wherein the chosen frequency for the ultrasonic sound wave is between 40 kHz and 1 MHz and the chosen modulation frequency is between 1 and 30 kHz.

5. The apparatus for remote, noninvasive characterization of an object as described in claim 1, wherein the object includes fluid-filled containers and pipes.

6. The apparatus for remote, noninvasive characterization of an object as described in claim 1, wherein said at least one air-coupled transducer is formed into an array having a geometry which focuses the ultrasonic sound wave onto the object to be characterized.

7. An apparatus for remote, noninvasive characterization of an object which comprises in combination:
    (a) at least one first air-coupled transducer for generating a first directed, ultrasonic sound wave having a chosen first frequency and directed toward the object to be characterized;
    (b) at least one second air-coupled transducer for generating a second directed, ultrasonic sound wave having a chosen second frequency, and directed toward the object to be characterized, whereby the first sound wave and the second sound wave are caused to intersect in a region in the air between said at least one first transducer and said at least one second transducer and the object to be characterized, such that the difference frequency therebetween is generated and impinges on the object to be characterized, thereby producing vibrational excitation in the object to be characterized; and
    (c) remote means for measuring the vibrational excitation in the object to be characterized, whereby the object is remotely characterized.

8. The apparatus for remote, noninvasive characterization of an object as described in claim 7, wherein said remote means for measuring the vibrational excitation includes a laser vibrometer.

9. The apparatus for remote, noninvasive characterization of an object as described in claim 7, wherein said at least one first air-coupled transducer and said at least one second air-coupled transducer are disposed at a sufficient distance from the object to be characterized such that a substantial portion of the first ultrasonic sound wave and the second ultrasonic sound wave are absorbed by the air therebetween after the difference frequency sound wave is generated.

10. The apparatus for remote, noninvasive characterization of an object as described in claim 7, wherein the chosen first frequency for the first ultrasonic sound wave is between 40 kHz and 1 MHz and the chosen second frequency for the second ultrasonic sound wave is between 40 kHz and 1 MHz, and the difference frequency is between 1 and 30 kHz.

11. The apparatus for remote, noninvasive characterization of an object as described in claim 7, wherein the object includes fluid-filled containers and pipes.

12. The apparatus for remote, noninvasive characterization of an object as described in claim 7, wherein said at least one first air-coupled transducer is formed into an array having a geometry which focuses the first directed, ultrasonic sound wave into the region of intersection of the first directed, ultrasonic sound wave and the second directed, ultrasonic sound wave, and wherein said at least one second air-coupled transducer is formed into an array having a geometry which focuses the second directed, ultrasonic sound wave into the region of intersection of the first directed, ultrasonic sound wave and the second directed, ultrasonic sound wave.

13. A method for remote, noninvasive characterization of an object which comprises the steps of:

(a) generating a directed, ultrasonic sound wave having a chosen frequency, wherein the ultrasonic sound wave is directed toward the object to be characterized;

(b) amplitude modulating the ultrasonic sound wave at a chosen modulation frequency, whereby the interaction of the amplitude modulated sound wave with the air medium generates a sound wave having as its frequency the chosen modulation frequency which produces vibrational excitation in the object to be characterized; and (c) remotely measuring the vibrational excitation in the object to be characterized, whereby the structure is remotely characterized.

14. The method for remote, noninvasive characterization of an object as described in claim 13, wherein the object includes fluid-filled containers and pipes.

15. The method for remote, noninvasive characterization of an object as described in claim 13, wherein the chosen frequency for the ultrasonic sound wave is between 40 kHz and 1 MHz and the chosen modulation frequency is between 1 and 30 kHz.

16. The method for remote, noninvasive characterization of an object as described in claim 13, wherein said step of generating a directed, ultrasonic sound wave having a chosen frequency is caused to occur at a sufficient distance from the object to be characterized that a substantial portion of the directed ultrasonic sound wave is absorbed by the air.

17. A method for remote, noninvasive characterization of an object which comprises the steps of:

(a) generating a first directed, ultrasonic sound wave having a chosen first frequency and directed toward the object to be characterized;

(b) generating a second directed, ultrasonic sound wave having a chosen second frequency, and directed toward the object to be characterized, whereby the first sound wave and the second sound wave are caused to intersect in the air such that the difference frequency therebetween is generated and impinges on the object to be characterized, thereby producing vibrational excitation in the object; and (c) measuring the vibrational excitation in the object to be characterized, whereby the object is remotely characterized.

18. The method for remote, noninvasive characterization of an object as described in claim 17, wherein the object includes fluid-filled containers and pipes.

19. The method for remote, noninvasive characterization of an object as described in claim 17, wherein the chosen first frequency for the first ultrasonic sound wave is between 40 kHz and 1 MHz and the chosen second frequency for the second ultrasonic sound wave is between 40 kHz and 1 MHz, and the difference frequency is between 1 and 30 kHz.

20. The method for remote, noninvasive characterization of an object as described in claim 17, wherein said step of generating a first directed, ultrasonic sound wave having a chosen first frequency and said step of generating a second directed, ultrasonic sound wave having a chosen second frequency are caused to occur at a sufficient distance from the object to be characterized that a substantial portion of the first ultrasonic sound wave and the second ultrasonic sound wave are absorbed by the air after the difference frequency sound wave is generated.

* * * * *